United States Patent
Pfersdorff

(10) Patent No.: US 10,509,214 B2
(45) Date of Patent: Dec. 17, 2019

(54) METHOD FOR DETECTING DEFECTS AND ASSOCIATED DEVICE

(71) Applicant: Soitec, Bernin (FR)

(72) Inventor: Olivier Pfersdorff, Laissaud (FR)

(73) Assignee: Soitec, Bernin (FR)

( * ) Notice: Subject to any disclaimer, the term of this patent is extended or adjusted under 35 U.S.C. 154(b) by 206 days.

(21) Appl. No.: 15/374,902

(22) Filed: Dec. 9, 2016

(65) Prior Publication Data
US 2017/0168279 A1   Jun. 15, 2017

(30) Foreign Application Priority Data
Dec. 11, 2015   (FR) ..................................... 15 62233

(51) Int. Cl.
*G02B 21/10*   (2006.01)
*G02B 21/00*   (2006.01)
(Continued)

(52) U.S. Cl.
CPC ......... *G02B 21/0016* (2013.01); *G02B 21/10* (2013.01); *G02B 21/26* (2013.01);
(Continued)

(58) Field of Classification Search
CPC ....... A61F 13/5622; G01B 11/30; G01B 9/04; G01N 2021/8822; G01N 2021/8874;
(Continued)

(56) References Cited

U.S. PATENT DOCUMENTS

| 6,157,444 A * | 12/2000 | Tomita | G01N 21/9501 356/237.1 |
| 6,724,947 B1 * | 4/2004 | Hayes | G06T 7/64 382/145 |

(Continued)

FOREIGN PATENT DOCUMENTS

| CN | 101629913 A | 1/2010 |
| CN | 103531497 B | 1/2017 |

(Continued)

OTHER PUBLICATIONS

Mann et al., Reducing disorder-induced losses for slow light photonic crystal waveguides through Bloch mode engineering, Optics Letters, 2013, pp. 4244-4247, vol. 38, No. 20, doi:10.1364/OL.38.004244.

(Continued)

*Primary Examiner* — Behrooz M Senfi
(74) *Attorney, Agent, or Firm* — TraskBritt

(57) ABSTRACT

A method for determining the size of a void-type defect in a top side of a structure comprising a top layer placed on a substrate, the defect being located in the top layer, includes introducing the structure into a reflected darkfield microscopy device in order to generate, from a light ray scattered by the top side, a defect-related first signal and a roughness-related second signal. The intensity of the roughness-related second signal is captured with a plurality of pixels. The intensity captured by each pixel is compared with the intensities captured by neighboring pixels. It is defined whether or not the pixel is contained in an abnormal zone.

(Continued)

The standard deviation of the intensity values captured by the pixels of the abnormal zone is extracted, and the size of the void-type defect associated with the abnormal zone is determined from the extracted standard deviation. A new device may be used for carrying out such a method.

17 Claims, 3 Drawing Sheets

(51) Int. Cl.
*G02B 21/26* (2006.01)
*G02B 21/36* (2006.01)
*G06K 9/46* (2006.01)
*G06T 7/00* (2017.01)
*H01J 37/28* (2006.01)
*H04N 5/225* (2006.01)

(52) U.S. Cl.
CPC ......... *G02B 21/365* (2013.01); *G06K 9/4604* (2013.01); *G06T 7/0004* (2013.01); *H01J 37/28* (2013.01); *H04N 5/2256* (2013.01)

(58) Field of Classification Search
CPC ....... G01N 2021/8928; G01N 21/4738; G01N 21/8851; G01N 21/9501; G02B 21/0016; G02B 21/10; G02B 21/26; G02B 21/365; G06K 9/4604; G06T 2207/10056; G06T 2207/20076; G06T 2207/30148; G06T 7/0004; H01J 37/28; H04N 5/2256
USPC .......................................................... 348/79
See application file for complete search history.

(56) References Cited

U.S. PATENT DOCUMENTS

| | | | | |
|---|---|---|---|---|
| 7,840,247 | B2* | 11/2010 | Liew | A61B 6/482 600/407 |
| 2002/0088952 | A1* | 7/2002 | Rao | G01N 21/9501 250/559.45 |
| 2004/0235206 | A1* | 11/2004 | Kuhlmann | G01N 21/9501 438/14 |
| 2006/0181700 | A1* | 8/2006 | Andrews | G01N 21/21 356/237.2 |
| 2008/0027665 | A1* | 1/2008 | Takahashi | G01N 21/8851 702/70 |
| 2009/0140180 | A1* | 6/2009 | Takahashi | G01N 21/9501 250/559.45 |
| 2011/0040168 | A1* | 2/2011 | Arnaud | G06T 7/0012 600/407 |
| 2011/0161014 | A1* | 6/2011 | Kim | G01N 21/9501 702/40 |
| 2011/0176718 | A1* | 7/2011 | Momonoi | G06T 7/001 382/145 |
| 2011/0181868 | A1* | 7/2011 | Stokowski | B82Y 10/00 356/51 |
| 2012/0019835 | A1* | 1/2012 | Nakao | G01N 21/8806 356/600 |
| 2013/0039471 | A1* | 2/2013 | Wormington | G01N 23/20 378/81 |
| 2015/0103351 | A1* | 4/2015 | Hess | G03F 1/84 356/445 |
| 2015/0131087 | A1* | 5/2015 | Ohtsubo | G01N 21/8806 356/237.5 |
| 2015/0377796 | A1* | 12/2015 | Schlezinger | H02S 50/00 356/72 |
| 2016/0305892 | A1* | 10/2016 | Tsuchiya | G01N 21/956 |
| 2019/0114464 | A1* | 4/2019 | Nicolle | G06K 9/00127 |

FOREIGN PATENT DOCUMENTS

| | | |
|---|---|---|
| CN | 104471484 B | 2/2018 |
| EP | 2128701 A1 | 12/2009 |

OTHER PUBLICATIONS

Chinese First Notification of Office Action and Search Report for Chinese Application No. 201611113931.8 dated Sep. 19, 2019, 12 pages.

* cited by examiner

METHOD FOR DETECTING DEFECTS AND ASSOCIATED DEVICE

PRIORITY CLAIM

This application claims the benefit of the filing date of French Patent Application Serial No. FR1562233, filed Dec. 11, 2015, for "METHOD FOR DETECTING DEFECTS AND ASSOCIATED DEVICE."

TECHNICAL FIELD

The present invention relates to the field of the inspection of defects located on the surface of a substrate. It in particular relates to a method for detecting and determining the size of void-type defects in a thin layer placed on a substrate, and to an associated device.

BACKGROUND

The method and device according to the present invention use a technique that is well known in the art to identify defects that are visible on the surface of a substrate. It is a question of reflected darkfield microscopy, the principle of which is schematically shown by way of example in FIG. 1.

This technique consists in projecting an incident light ray 1 onto the surface of a substrate 4, for example, obliquely, at an angle β with respect to a plane P, parallel to the surface of the substrate to be observed. According to prior-art embodiments, it is also possible to project the light ray 1 perpendicularly to the surface of a substrate 4 (also called normal mode). The incident light ray 1 is thus directed in the direction of the surface of the substrate 4, for example using planar and/or concave mirrors 2, 3 allowing it to be concentrated on the surface of the substrate 4. Therefore, if the surface of the substrate to be observed were a defect-free planar mirror, the incident light ray 1 would be entirely reflected by the surface of the substrate 4 at the same angle β (called the "β" reflected ray and referenced by the reference 1' in FIG. 1). Thus in this case, since the incident light ray 1 is not deviated, no light is scattered in the direction of a collecting channel 5 at the end of which a detecting unit 6 (such as a photomultiplier) is located; the latter detects the light intensity of a light ray scattered (i.e., reflected off the path of the "β" reflected ray 1') by the surface of the substrate 4. In such a case, the detecting device will capture a uniform dark image.

In the case where the surface of the substrate 4 to be observed includes defects, some of the incident light ray 1 illuminating the surface of the substrate 4 is scattered by the defects in the direction of the collecting channel 5. The detecting unit 6 thus captures the light intensity thereof, which is converted into digital data, then transmitted to a data-processing means in order to be displayed, for example, on a screen 7. The obtained image is a representation in which the defects located on the surface of the substrate 4 appear light on a dark background.

It will be recalled that reflected darkfield illumination is particularly recommended for the study of surfaces. Reflected darkfield microscopy allows the amount of directly transmitted light to be minimized and only light deviated or scattered by defects located on the surface of the substrate 4 to be collected. It thus allows the contrast of the image illustrating the defects to be considerably increased while requiring relatively little equipment and simple preparation of the substrate 4. However, this technique suffers from the low light intensity collected and is always affected by a resolution limit.

An important field of application of this type of technology is the field of microelectronics. Specifically, in the semiconductor industry, reflected darkfield microscopy is used to inspect the surfaces of substrates, especially in order to detect particulates generated by various sources of contamination. Constantly progressing, this industry requires increasingly high product quality levels. By virtue of darkfield illumination, which is used in many pieces of metrology equipment, it is possible to detect particulates of size smaller than 0.1 microns, especially on silicon substrates.

Fully depleted semiconductor-on-insulator (FDSOI) (e.g., FD silicon-on-insulator) structures are increasingly used as substrates for the fabrication of components. In addition to surface particulates, other types of defects may be located in the silicon top layer forming the useful layer of the SOI structure; void-type defects, i.e., defects corresponding to zones devoid of the useful top layer, may especially be present in the top layer. To guarantee the quality level of SOI structures, it is essential to be able to identify and classify defects of this type that are smaller than 500 microns in size (defects of size larger than 500 microns being identifiable by other visual inspection techniques). Furthermore, since the required quality level continues to increase, the classification of defects smaller than 250 microns diameter, or even 100 microns diameter, may even be necessary in the near future. These defects, which are specific to SOI structures, have a signature in terms of the scattered light ray that is different from that of particulates.

The document US2004/0235206 discloses apparatus and methods for specimen inspection, to be applied to a bare substrate or a film stack deposited on a substrate. The method enables robust separation between signals of interest (for defects detection) and noise. Nevertheless, it does not allow the classification of the size of specific void-type defect.

Generally speaking, prior-art solutions do not allow void-type defects to be classed by size. Current measurements, which are obtained by virtue of pieces of metrology equipment intended to measure and count particulates, yield very imprecise classification results, thereby preventing SOI structures from being reliably sorted by the size of these "void" defects, to quantify their quality level.

BRIEF SUMMARY

One objective of the invention is therefore to provide a detecting method obviating the drawbacks of the prior art. One objective of the invention is especially to provide a method and device for inspecting SOI structures allowing void-type defects located in the useful top layer to be detected and classified by size.

The present invention relates to a method for determining the size of a void-type defect in a top side of a structure comprising a top layer placed on a substrate, the defect being located in the top layer; the method comprising:
  a) a step of introducing the structure into a reflected darkfield microscopy device in order to generate, from a light ray scattered by the top side, a defect-related first signal and a roughness-related second signal; and
  b) a step of capturing, with a plurality of pixels, the intensity of the roughness-related second signal.

The method is noteworthy in that it furthermore comprises:

c) a processing step for comparing the intensity captured by each pixel with the intensities captured by neighboring pixels and for defining whether the pixel is contained in an abnormal zone;

d) a step of extracting the standard deviation of the intensity values captured by the pixels of the abnormal zone; and e) a step of determining the size of the void-type defect associated with the abnormal zone, from the extracted standard deviation.

The method according to the invention thus allows, from a specific attribute of the abnormal zone (the standard deviation of the intensity values captured by the pixels contained in the abnormal zone), the size of void-type defects to be determined.

According to advantageous features of the invention, which features may be implemented alone or in combination:

the scattered light ray is generated by reflection, from the top side of the structure, of an incident light ray of oblique direction with respect to a plane parallel to the face;

the structure is moved along at least one translational axis and/or about at least one rotational axis under the incident light ray to allow the capturing step b);

each pixel may measure between 20 microns and 1000 microns in side length;

the determining step is carried out by applying a correlation curve relating the standard deviation and size of the void-type defects;

the size of void-type defects is measured in structures by scanning electron microscopy to establish the correlation curve;

the correlation curve is applicable to void-type defects the size of which is comprised between 5 and 500 microns;

the processing step defines that a given pixel is contained in the abnormal zone when the ratio of the intensity captured by the given pixel to the intensity captured by at least one neighboring pixel is higher than a preset factor;

the pixels neighboring the given pixel are comprised in a zone peripheral to the pixel and having an annular shape;

the annular shape has an inside diameter of 600 microns and an outside diameter of 2500 microns.

The invention also relates to a device for detecting a void-type defect in a top side of a structure comprising a top layer placed on a substrate, the defect being located in the top layer; the device comprises:

a reflected darkfield microscopy apparatus configured to project an incident light ray in the direction of the top side of the structure and to collect a light ray scattered by the top side; and a detecting unit configured to generate, from the scattered light ray, a defect-related first signal and a roughness-related second signal, and to capture, with a plurality of pixels, the intensity of the roughness-related second signal.

The device is noteworthy in that it comprises:

a first processing unit that is connected to the detecting unit, and configured to compare the intensity captured by each pixel with the intensities captured by neighboring pixels, and to define whether the pixel is contained in an abnormal zone;

a second processing unit that is configured to extract the standard deviation of the values of the intensities captured by the pixels of the abnormal zone; and a correlation curve for determining the size of the void-type defect associated with the abnormal zone, from the extracted standard deviation.

BRIEF DESCRIPTION OF THE DRAWINGS

Other features and advantages of the invention will become apparent from the following detailed description of the invention given with reference to the appended figures, in which.

DETAILED DESCRIPTION OF THE INVENTION

Known prior-art defect inspection techniques employing a reflected darkfield microscopy device do not allow the size of void-type defects (and more particularly void-type defects that are smaller than 500 μm in diameter) present in the top layer of SOI structures in particular, to be determined with precision. It will be recalled that an SOI structure comprises a top layer placed on a carrier substrate; the defects that it is sought to detect are voids in this top layer.

Nonlimitingly, possible embodiments of the device and method for detecting defects according to the invention, and allowing the aforementioned issues to be mitigated, will now be described with reference to FIGS. 2 to 5, respectively.

Figure 1:
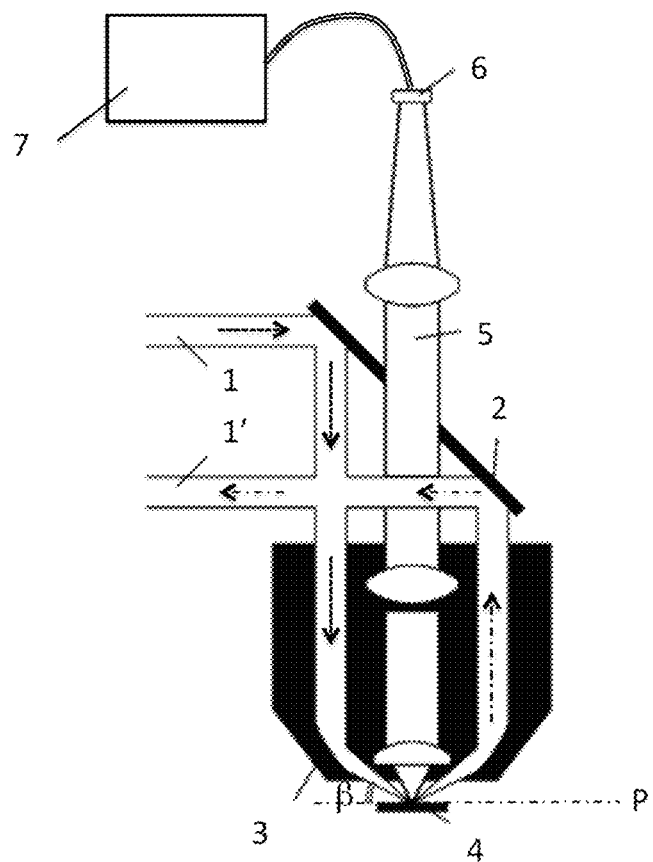
FIG. 1 shows a schematic view of a known prior-art reflected darkfield microscopy device.
Figure 2:
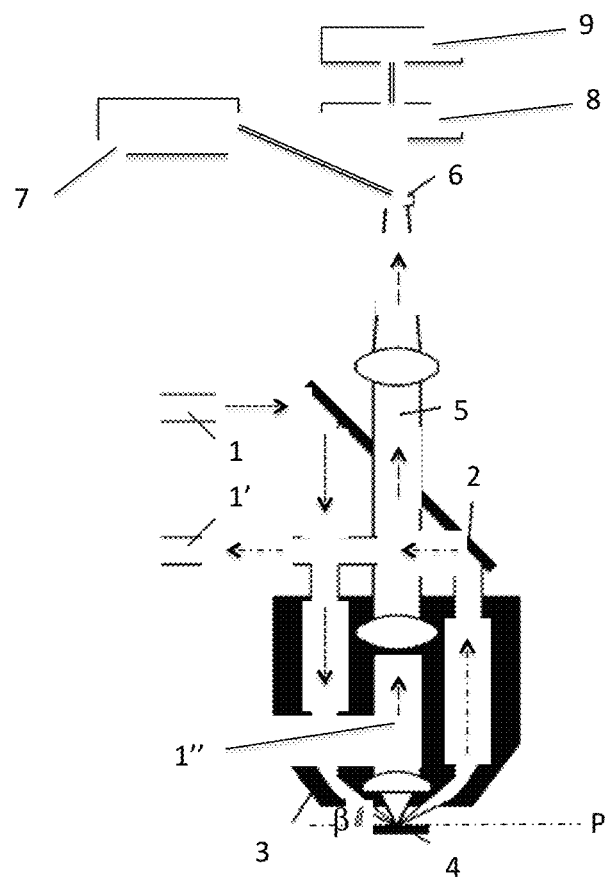
FIG. 2 shows a schematic view of the device for detecting defects according to the invention.

As described above, reflected darkfield microscopy consists in illuminating the top side of a structure 4 using at least one incident light ray 1 directed at a defined angle $\beta$ with respect to a plane P parallel to the top side of the structure 4 to be observed, such as illustrated in FIG. 2. The angle $\beta$ is comprised between 0 and 90°. According to embodiments, the incident light ray 1 may be configured to partially or completely scan the top side of the structure 4. Advantageously, the structure 4 is moved along at least one translational axis and/or about at least one rotational axis under the incident light ray 1, in order to allow all or some of its top side to be inspected. The light ray 1 is thus directed in the direction of the top side, for example, using a first series of one or more planar and/or concave mirrors 2, 3 allowing the incident light ray 1 to be oriented and concentrated on the surface to be analyzed. Nonlimitingly, the light ray 1 may for example be a laser beam.

The surface of the structure 4 may include one or more smooth defect-free planar zones and one or more zones comprising at least one defect (particulate, void-type defect, roughness, etc.).

In the case where the light ray 1 is directed onto a smooth planar zone, it is entirely reflected at the same angle $\beta$ as that defined by the orientation of the incident light ray 1 with respect to the plane P. Thus, the light ray 1 is not deviated from its path and is removed from the device (reflected ray 1') using a second series of planar and/or concave mirrors 2, 3.

In the case where the light ray 1 strikes a zone comprising at least one defect or a rough zone, at least some of the light ray 1 is reflected (light ray 1") by the defect in the direction of a collecting channel 5. Such a reflection is essentially diffuse because the incident light ray 1 is reflected in many directions. In the rest of the present description, the light ray reflected by a defect in/on the surface of the structure 4 will be called the scattered light ray 1".

A detecting unit 6 such as a photomultiplier is located at the end of the collecting channel 5; the unit detects the intensity of the scattered light ray 1". Nonlimitingly, the observing channel 5 may include one or more optical filters and/or lenses for directing, concentrating or filtering the light ray 1" scattered toward the photomultiplier 6, depending on the requirements of the application of the detecting device according to invention.

Another functionality, known in the prior art, of the photomultiplier 6 consists in decomposing the captured scattered light ray 1" into two signals, a defect-related first signal and a roughness-related second signal. The first signal especially allows type A defects (namely, for example, particulates or other defects that protrude from the surface of the substrate) to be detected. The roughness-related second signal especially allows type B defects (for example, the roughness level of the surface of the structure 4, etc.) to be detected and is commonly called the "haze" signal. The decomposition of the intensity of the scattered light ray 1" into a defect-related first signal and a roughness-related second signal depends on sensitivity thresholds defined depending on the size of the type A defects and/or on the roughness level that it is desired to measure, on the optical filters used (if any), and on the material from which the top layer of the structure 4 is made.

The photomultiplier 6 is associated with an array of a plurality of pixels. Nonlimitingly, a pixel, conventionally of square shape, may measure between 20 μm and 1000 μm in side length. In the present embodiment and by way of example, each pixel measures 200 μm×200 μm.

According to the present invention, it is not the type-A-defect first signal but the roughness-related second signal that is used to further characterize the void-type defect of interest.

Thus, the intensity of the (roughness-related) second signal may be captured by each pixel of the photomultiplier 6 in order to be converted into a numerical datum characteristic of the intensity. It is thus possible to obtain an image, from the plurality of pixels, of B type defects (the roughness or "haze"), which image is transmitted directly to a displaying device 7 so as to display the defects, for example, on a screen.

The photomultiplier 6 of the device according to the invention transmits the roughness-related second signal to a first processing unit 8. The role of this first unit 8 is to compare the intensity of the second signal captured by each pixel with the intensities captured by the neighboring pixels in order to define whether the pixel forms part of an abnormal zone.

The first processing unit 8 defines that a given pixel is contained in an abnormal zone when the ratio of the intensity captured by the given pixel to the intensity captured by at least one neighboring pixel is higher than a preset factor. The neighbors of a given pixel are all the pixels comprised in a peripheral zone having an annular shape with the given pixel as its center. Advantageously, the inside diameter of the annular shape is 600 microns and the outside diameter of the annular shape is 2500 microns. The preset factor may for example vary between 1 and 20 and advantageously between 2 and 10. By way of example, it is equal to 4; in this case an abnormal zone includes at least one pixel capturing a light intensity four times more intense than one of its neighboring pixels.

In the presence of a void-type defect, the intensity of the captured roughness-related second signal will vary from one pixel to the next. In particular, since the border of this type of defect consists in a step or a plurality of step levels between the surface of the top layer and the surface of the subjacent substrate, the intensity of the second signal associated with rays scattered in this location will be higher than the intensity of the second signal associated with rays scattered in a planar neighboring zone of the top layer. In the same way, since the central portion of the void-type defect is deeper than its border, the intensity of the second signal associated with rays scattered in this location will be higher than the intensity at the border. It is these intensity differences between neighboring pixels that allow an abnormal zone to be defined.

Figure 3:
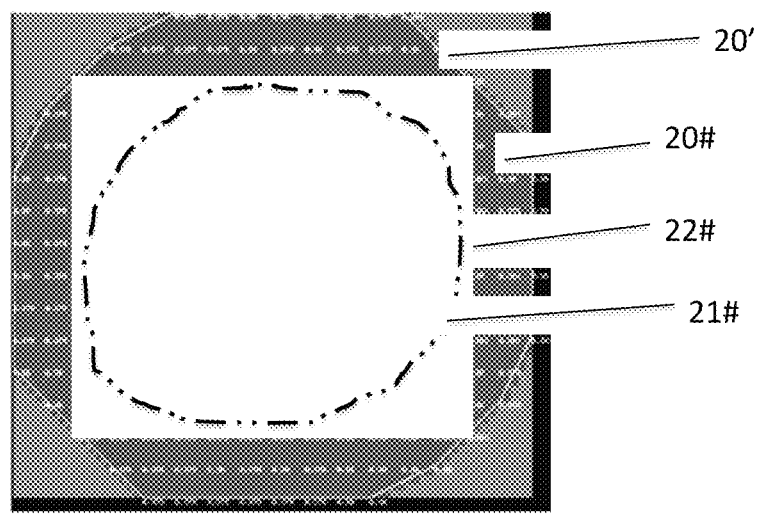
FIG. 3 shows an example of a defect detected by virtue of the device and using the method according to the invention.
Figure 4:
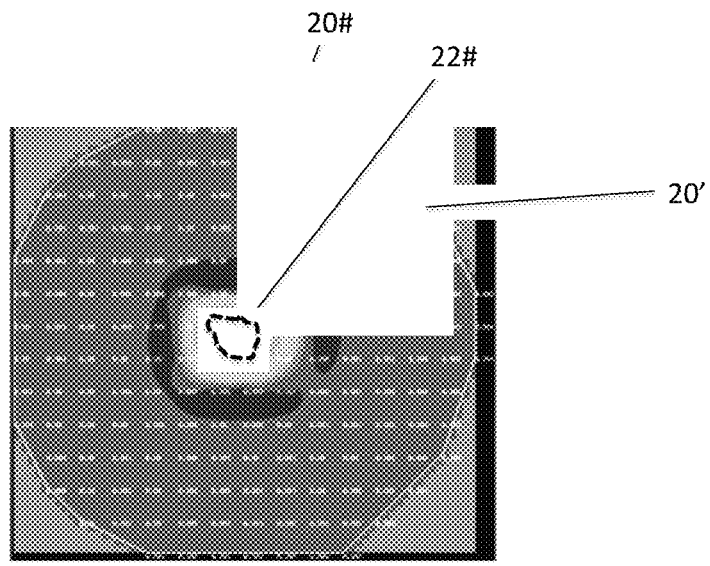
FIG. 4 shows another example of a defect detected by virtue of the device and using the method according to the invention.

FIGS. 3 and 4 show illustrations of abnormal zones 20 identified in the top side of a structure 4. The abnormal zone 20 comprises all the area inside the outline 20'.

Each abnormal zone 20 indicates the presence of a void-type defect located in the top layer of the structure 4. The area of the abnormal zone 20 could be extracted; nevertheless, this value correlates poorly with the actual size of the defect, which size is defined by the outline 21.

In FIGS. 3 and 4, each value collected in the abnormal zone 20 is an indication of the intensity of the roughness-related second signal of the scattered light ray 1" captured by one pixel. By way of example, the pixels in the central portions (e.g., within outline 22) of the abnormal zones 20 have (normalized) values of 13 ppm; the borders of the defect (between the outline 22 and the outline 21 illustrated in FIG. 3) exhibit a gradual decrease in intensity ((normalized) values between 0.4 and 5 ppm, for example) indicating a variation in the depth of the defect. In the portion peripheral to the defect, in the abnormal zone 20 (outside the outline 21 illustrated in FIG. 3), the (normalized) values are lower than 0.4 ppm.

The applicant has extracted the standard deviation of the values from a number of identified abnormal zones 20 and has demonstrated a good correlation with the actual size of the associated void-type defect, the actual size of the defect having been measured, moreover, by a reliable measurement technique (scanning electron microscopy for example). This correlation, which was not obvious at first, is due to the fact that, in an abnormal zone 20, the number of pixels for which the intensity value is high increases with the size of the void-type defect. Thus, the standard deviation of the distribution of the intensity values in an abnormal zone increases as the size of the void-type defect increases: the standard deviation is influenced by the number of high values, which will tend to widen the profile of the distribution.

Figure 5:
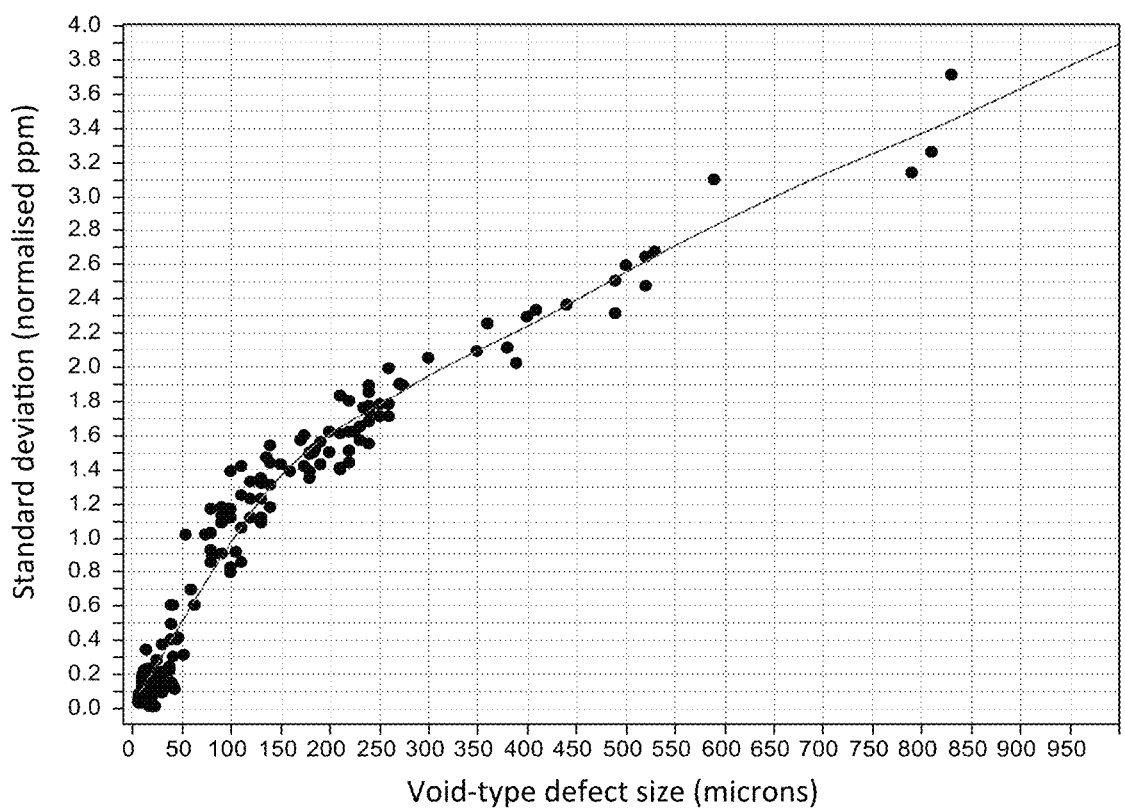
FIG. 5 shows the correlation curve between the defect size and the standard deviation of the values of the intensity captured by the pixels contained in an abnormal zone.

FIG. 5 shows a correlation curve between the standard deviation of the intensity values of the second signal of the scattered light ray 1" and the void-type-defect size. Extraction of the standard deviations of the normalized values (which are representative of the intensity of the second signal of the scattered ray) collected in the abnormal zones 20 in FIGS. 3 and 4 (5.34 ppm and 1.84 ppm, respectively) allowed the size of the void-type defects (1260 microns and 250 microns, respectively) to be determined from the correlation curve.

In the example in FIG. 5, pixels of 200×200 microns were used; it may be noted that the correlation limit is for defect sizes of about 50 microns and less. If smaller pixel sizes were used (20 microns for example), the correlation curve would possibly demonstrate a good correlation down to defect sizes of about 5 microns. It would also demonstrate a more precise correlation between the standard deviation and the size of the void-type defects.

Using the device for detecting and the method for determining the size of void-type defects of the invention, it is possible to define the size of a void-type defect with a level of precision of about ±15% for defects of size larger than about 5 µm.

The device according to the invention therefore advantageously includes a second processing unit 9, which is connected to the first processing unit, allowing the standard deviation of the intensity values captured by the pixels contained in the abnormal zone 20 to be extracted. These values may then be correlated to the actual size of the void-type defect associated with the identified abnormal zone 20 by virtue of application of the correlation curve or table. It may also include a unit 7 for displaying the image of the abnormal zone 20 corresponding to a void-type defect located in the top side of the structure 4, the defect for example appearing light on a dark background.

Advantageously, the device according to the invention may be connected to an automatic sorting device that, on the basis of the void-type-defect sizes (determined from the standard deviation of the intensities in each abnormal zone identified in the structure 4), will establish a quality level of the structure 4.

The device and method according to the invention allow the surface finish of a structure 4 to be inspected, the size of void-type defects in the top layer to be determined and thus, a quality level relative to the size of these defects to be defined.

Of course, the invention is not limited to the described embodiments and variant embodiments may be implemented without departing from the scope of the invention as defined by the claims.

What is claimed is:

1. A method for determining a size of a void-type defect in a top side of a structure comprising a top layer placed on a substrate, the defect being located in the top layer, the method comprising:
    a) a step of introducing the structure into a reflected darkfield microscopy device in order to generate, from a light ray scattered by the top side, a defect-related first signal and a roughness-related second signal; and
    b) a step of capturing, with a plurality of pixels, the intensity of the roughness-related second signal;
    c) a processing step including comparing the intensity captured by each pixel with the intensities captured by neighboring pixels and defining whether the pixel is contained in an abnormal zone;
    d) a step of extracting the standard deviation of the intensity values captured by the pixels of the abnormal zone; and
    e) a step of determining the actual size of the void-type defect associated with the abnormal zone, from the extracted standard deviation of the intensity values captured by the pixels contained in the abnormal zone, the determining step being carried out by applying a correlation curve relating the standard deviation of the intensity values captured by the pixels contained in the abnormal zone and size of the void-type defects.

2. The method of claim 1, wherein the scattered light ray is generated by reflection, from the top side of the structure, of an incident light ray of oblique direction with respect to a plane parallel to the face.

3. The method of claim 2, wherein the structure is moved along at least one translational axis and/or about at least one rotational axis under the incident light ray to allow the capturing step b).

4. The method of claim 3, wherein each pixel measures between 20 microns and 1000 microns in side length.

5. The method of claim 1, further comprising measuring the size of void-type defects in a plurality of structures using scanning electron microscopy to establish the correlation curve.

6. The method of claim 1, wherein the correlation curve is applicable to void-type defects having sizes between 5 microns and 500 microns.

7. The method of claim 1, wherein the processing step defines that a given pixel is contained in the abnormal zone when the ratio of the intensity captured by the given pixel to the intensity captured by at least one neighboring pixel is higher than a preset factor.

8. The method of claim 7, wherein the pixels neighboring the given pixel are located in a zone peripheral to the pixel and having an annular shape.

9. The method of claim 8, wherein the annular shape has an inside diameter of 600 microns and an outside diameter of 2500 microns.

10. The method of claim 1, wherein each pixel measures between 20 microns and 1000 microns in side length.

11. A method for determining a size of a void-type defect in a top semiconductor layer of a semiconductor-on-insulator semiconductor substrate, comprising:
    introducing the semiconductor-on-insulator semiconductor substrate into a reflected darkfield microscopy device and generating, from a light ray scattered by the top semiconductor layer, a defect-related first signal and a roughness-related second signal;
    capturing, with pixels, the intensity of the roughness-related second signal;
    comparing the intensity captured by each of the pixels with the intensities captured by neighboring pixels and defining whether each pixel is contained in an abnormal zone;
    determining a standard deviation of the intensity values captured by each pixel contained in the abnormal zone; and
    determining the actual size of the void-type defect associated with the abnormal zone from the determined standard deviation of the intensity values captured by the pixels contained in the abnormal zone, by applying a correlation curve relating the standard deviation of the intensity values captured by the pixels contained in the abnormal zone and size of the void-type defects.

12. The method of claim 11, wherein the scattered light ray is generated by reflection, from the top semiconductor layer, of an incident light ray oriented at an oblique direction relative to a plane parallel to a surface of the top semiconductor layer.

13. The method of claim 12, further comprising moving the semiconductor-on-insulator semiconductor substrate along at least one translational axis and/or about at least one rotational axis under the incident light ray to allow the capturing of the intensity of the roughness-related second signal.

14. The method of claim 11, wherein each pixel measures between 20 microns and 1000 microns in side length.

15. The method of claim 11, wherein the correlation curve is applicable to void-type defects having sizes between 5 microns and 500 microns.

16. The method of claim 1, wherein defining whether each pixel is contained in an abnormal zone comprises defining that a given pixel is contained in the abnormal zone when the ratio of the intensity captured by the given pixel to the intensity captured by at least one neighboring pixel is higher than a preset factor between 1 and 20.

17. A device for detecting a void-type defect in a top side of a structure comprising a top layer placed on a substrate, the defect being located in the top layer, the device comprising:
- a reflected darkfield microscopy apparatus configured to project an incident light ray in the direction of the top side of the structure and to collect a light ray scattered by the top side;
- a detecting unit configured to generate, from the scattered light ray, a defect-related first signal and a roughness-related second signal, and to capture, with a plurality of pixels, the intensity of the roughness-related second signal;
- a first processing unit that is connected to the detecting unit, and configured to compare the intensity captured by each pixel with the intensities captured by neighboring pixels, and to define whether the pixel is contained in an abnormal zone;
- a second processing unit that is configured to extract the standard deviation of the values of the intensities captured by the pixels of the abnormal zone; and
- a correlation curve for determining the actual size of the void-type defect associated with the abnormal zone, from the extracted standard deviation of the intensity values captured by the pixels contained in the abnormal zone, the correlation curve relating the standard deviation of the intensity values captured by the pixels contained in the abnormal zone and size of the void-type defects.

\* \* \* \* \*